(12) United States Patent
Cichocki, Jr. et al.

(10) Patent No.: US 10,448,947 B2
(45) Date of Patent: *Oct. 22, 2019

(54) SWAGING SYSTEMS FOR ATTACHING SURGICAL NEEDLES TO SUTURES HAVING ON-PRESS TESTING OF SUTURE ATTACHMENT STRENGTH

(71) Applicant: Ethicon, Inc., Somerville, NJ (US)

(72) Inventors: Frank Richard Cichocki, Jr., Easton, PA (US); Alexander M. Cannara, Roseland, NJ (US)

(73) Assignee: Ethicon, Inc., Somerville, NJ (US)

( * ) Notice: Subject to any disclaimer, the term of this patent is extended or adjusted under 35 U.S.C. 154(b) by 315 days.

This patent is subject to a terminal disclaimer.

(21) Appl. No.: 15/465,912

(22) Filed: Mar. 22, 2017

(65) Prior Publication Data

US 2018/0271518 A1    Sep. 27, 2018

(51) Int. Cl.
*A61B 17/06* (2006.01)
*B21J 9/06* (2006.01)
(Continued)

(52) U.S. Cl.
CPC .......... *A61B 17/06004* (2013.01); *B21G 1/00* (2013.01); *B21J 9/06* (2013.01);
(Continued)

(58) Field of Classification Search
CPC .............. A61B 17/06004; A61B 17/06; A61B 17/06061; B21D 39/04; B21D 39/046;
(Continued)

(56) References Cited

U.S. PATENT DOCUMENTS 3,875,946 A * 4/1975 Duncan ............ A61B 17/06004
163/1
3,890,975 A * 6/1975 McGregor ....... A61B 17/06004
163/1
(Continued)

FOREIGN PATENT DOCUMENTS

CA           1022734      12/1977
EP           0663187       7/1995
(Continued)

OTHER PUBLICATIONS

Janome:"Janome Industrial Equipment USA,Inc. Home", Mar. 8, 2017 (Mar. 8, 2017), XP055466470, janomeie.com Retrieved from the Internet: URL:http://web.archive.org/web/20170308080728/ http://www.janomeie.com:80/products/electro press/jps series/spec. html [retrieved on Apr. 11, 2018], p. 3.

(Continued)

*Primary Examiner* — Tyrone V Hall, Jr.

(57) ABSTRACT

A swaging system for attaching surgical needles to sutures and testing the attachment strength includes a frame, a bottom swaging die mounted on the frame, and a top swaging die mounted on the frame and being moveable up and down along a swaging axis that is aligned with the bottom swaging die. The bottom swaging die includes a hinge mechanism with a bottom plate mounted to the frame and a top plate overlying the bottom plate. The top and bottom plates are pivotally connected for enabling the top plate to pivot relative to the bottom plate. The bottom swaging die includes a swaging tool that extends toward the top swaging die along the swaging axis, and a load cell disposed between the top and bottom plates for monitoring load. The system includes a control system having one or more pull test programs stored therein for evaluating pull (Continued)

tests on armed surgical needles to determine if the armed surgical needles are acceptable or unacceptable.

20 Claims, 12 Drawing Sheets

(51) Int. Cl.
| | |
|---|---|
| *G01N 3/08* | (2006.01) |
| *B21G 1/00* | (2006.01) |
| *A61B 17/00* | (2006.01) |
| *B21K 25/00* | (2006.01) |

(52) U.S. Cl.
CPC ...... *G01N 3/08* (2013.01); *A61B 2017/00119* (2013.01); *A61B 2017/00526* (2013.01); *A61B 2017/00946* (2013.01); *A61B 2017/06028* (2013.01); *B21K 25/00* (2013.01)

(58) Field of Classification Search
CPC .... B25B 27/10; F16L 13/46; F16L 2013/145; Y10T 29/53987; Y10T 29/5367; Y10T 29/53796
See application file for complete search history.

(56) References Cited

U.S. PATENT DOCUMENTS

| | | | | |
|---|---|---|---|---|
| 3,980,177 | A * | 9/1976 | McGregor | A61B 17/06004 206/63.3 |
| 4,613,800 | A | 9/1986 | Jeppsson | |
| 5,092,026 | A | 3/1992 | Klemmer et al. | |
| 5,383,902 | A * | 1/1995 | Carpentiere | A61B 17/06004 606/222 |
| 5,394,971 | A * | 3/1995 | Colligan | A61B 17/06004 198/345.1 |
| 5,438,746 | A * | 8/1995 | Demarest | A61B 17/06004 163/1 |
| 5,487,216 | A * | 1/1996 | Demarest | A61B 17/0467 29/705 |
| 5,500,991 | A | 3/1996 | Demarest et al. | |
| 5,623,189 | A | 4/1997 | Hemmer | |
| 5,707,391 | A * | 1/1998 | Carpentieri | A61B 17/06004 29/515 |
| 5,793,634 | A | 8/1998 | Demarest et al. | |
| 5,844,142 | A * | 12/1998 | Blanch | A61B 17/06004 73/827 |
| 5,903,966 | A * | 5/1999 | Sonderegger | A61B 17/06004 29/464 |
| 5,918,284 | A | 6/1999 | Blanch et al. | |
| 5,920,482 | A | 7/1999 | Demarest et al. | |
| 5,943,765 | A * | 8/1999 | Shikakubo | A61B 17/06004 29/243.517 |
| 5,948,997 | A | 9/1999 | Schmidt | |
| 6,016,682 | A * | 1/2000 | Tannhauser | A61B 17/06004 163/1 |
| 6,058,821 | A * | 5/2000 | Demarest | A61B 17/0467 83/385 |
| 6,081,981 | A * | 7/2000 | Demarest | A61B 17/06004 29/407.04 |
| 6,647,803 | B1 | 11/2003 | Demarest et al. | |
| 6,845,645 | B2 | 1/2005 | Bartrom et al. | |
| 7,185,411 | B2 | 3/2007 | Lenihan et al. | |
| 8,214,996 | B2 * | 7/2012 | Stametz | A61B 17/06004 163/5 |
| 2008/0119876 | A1 * | 5/2008 | Price | A61B 17/06004 606/144 |
| 2018/0272416 | A1 * | 9/2018 | Cannara | B21J 9/20 |

FOREIGN PATENT DOCUMENTS

| | | |
|---|---|---|
| EP | 0875207 | 11/1998 |
| JP | 3024773 | 3/2000 |
| JP | 2013081885 | 5/2013 |

OTHER PUBLICATIONS

Janome: "Janome JP-S Series—New Generation Servo Press", Sep. 9, 2016 (Sep. 9, 2016), XP055466520, Retrieved from the Internet: URL:http://temas.vn/Uploads/documents/Unipulse/Servo%20press%20JP-S.pdf.pdf [retrieved on Apr. 11, 2018].

International Search Report issued in corresponding International Application No. PCT/US2018/017551, dated Apr. 24, 2018, 5 pages.

International Search Report issued in International Application No. PCT/US2018/017560, dated Apr. 30, 2018, 5 pages.

SMAC Moving Coil Actuators, SMAC Corporation of Carlsbad, California, www.smac-mca.com/technical-resources/moving-coil-technology, 2017, 2 pages.

\* cited by examiner

SWAGING SYSTEMS FOR ATTACHING SURGICAL NEEDLES TO SUTURES HAVING ON-PRESS TESTING OF SUTURE ATTACHMENT STRENGTH

BACKGROUND OF THE INVENTION

Field of the Invention

The present patent application is generally related to swaging systems for attaching surgical needles to sutures, and is more particularly related to systems, devices and methods for testing the strength of needle and suture attachments.

Description of the Related Art

Armed surgical needles, i.e., needles having sutures attached to one end thereof, are typically manufactured utilizing manual, semi-automated, and fully automated procedures that feed a length of suture material into a suture receiving opening of a surgical needle, and that swage (i.e., compress) the surgical needle to the end of the suture.

Swaging needles to sutures typically involves inserting the free end of a suture into an axial bore of a needle barrel of a surgical needle, and holding the suture inside the axial bore while a swage die impinges upon the outer surface of the needle barrel, thereby compressing a portion of the bore onto the suture. The compressed portion of the axial bore grasps the suture by mechanical interference and by surface friction. The swaging process is conducted to create an attachment between the needle barrel and the suture that meets or exceeds "pull-out" strength standards.

FIG. 1 illustrates a prior art method of swaging a needle N to a suture S utilizing a single-sided, multiple indentation swaging protocol. The suture S is inserted into a suture receptacle SR of the needle N, and at least one stake point of a die is driven into one side of the needle N to deform the wall W of the needle and create a depression $D_1$ that causes the wall W to impinge upon the suture S, creating a pressure point $P_1$ between the depression $D_1$ and the opposing portion of the needle wall W. One or more additional indentations $D_2$ can be made to create additional pressure points, e.g. $P_2$. The suture S is retained in the needle N by virtue of the impingement of a small portion of the needle wall W on a correspondingly limited area of the suture S.

FIG. 2 illustrates another prior art method of swaging a needle N to a suture S utilizing a double-sided, aligned swaging protocol. The suture S is inserted within a suture receptacle SR of a needle N, and two opposing stakes are utilized to create aligned depressions $D_3$, $D_4$ that form a pressure point $P_3$ between the two depressions, $D_3$, $D_4$ for grasping the suture S. The focused pressure at $P_3$ may create sheer stress that could result in fracturing of the suture S, leading to suture detachment. To avoid exceeding the sheer stress limits of the suture material, the dimensions of the suture receptacle SR, the thickness and deformability of the wall W of the needle N, and the depression depth of the depressions $D_3$ and $D_4$ are controlled.

FIG. 3 shows a prior art needle swaging assembly 20 with first and second swage dies 22A, 22B converging to hold a needle N for swaging. The needle N is gripped between needle holders 24A, 24B and abuts against needle stops 26A, 26B with the suture receptacle SR aligned with the suture grooves 28A, 28B. Insertion of the needle N between the needle holders 24A, 24B is facilitated by needle funnel portions 30A, 30B. A suture funnel 32 aides in threading the suture S through the suture grooves 28A, 28B and into the suture receptacle SR of the needle N. Swaging elements 34A, 34B are free to slide within respective slots 36A, 36B so that the stakes 38A, 38B thereof can impinge upon the needle N. In the embodiment shown in FIG. 3, the stakes 38A are laterally offset relative to the stakes 38B such that when the swaging elements 34A, 34B are urged together during the swaging operation, the needle N will be swaged to create a serpentine configuration in the suture receptacle SR. A greater or lesser number of stakes 38A, 38B may be utilized, ranging from one stake 38A, 38B on each swaging element 34A, 34B, up to any selected number of stakes 38A, 38B. The height, spacing and shape of the stakes 38A, 38B, as well as the relative lateral offset of the stakes 38A, 38B on opposite swaging elements 34A, 34B may be selected to adjust swaging and suture attachment strength.

One approach to providing good suture attachment is multiple hit swaging, wherein a needle is subjected to swaging of a controlled depth, however, the compression is distributed over a large area of the needle barrel (e.g., around the circumference of the needle barrel). To achieve this type of swaging, the needle may be rotated relative to the swaging dies between multiple swaging compressions. In this manner, multiple angularly offset swaging operations are performed to attach a single needle to a single suture. While this approach provides a reliable attachment, each hit on the barrel of the needle produces stress in the needle barrel and the suture. The needle and suture materials have some degree of malleability, but when the limit of malleability is reached, the materials will fail, leading to, in the case of the needle, cracking and loss of attachment, or breakage. Cracking is a particular problem when harder alloys are used, including advanced alloys such as 4310 SS, nickel-titanium SS, and 420 SS. Further, needle materials have some elasticity, such that the relief of residual stress causes the needle barrel to relax over time, leading to a loss of attachment between the needle bore and the suture.

One advance directed to minimize failure of the parts during a swaging operation is disclosed in commonly assigned U.S. Pat. No. 8,214,996 to Stametz et al., the disclosure of which is hereby incorporated by reference herein. In one embodiment, the '996 patent discloses a method of attaching a suture to a needle barrel. In one embodiment, a first compression stroke compresses a radial top of a needle barrel against a suture that has been inserted into a bore of the needle barrel while restraining the radial bottom and radial sides of the needle barrel against deformation. A second compression stroke compresses the bottom of the barrel against the suture while restraining the sides against deformation. In another embodiment, the top and bottom sides of a needle barrel are compressed while the opposing lateral sides of the needle barrel are restrained against deformation. In one embodiment, an apparatus for attaching a suture to a needle barrel includes two die sets, each including a die with a groove therein. In one die set, the groove protects the bottom and lateral sides of the needle barrel from deformation while the top is compressed. In the other die set, the groove protects the lateral sides of the needle barrel from deformation while the bottom of the needle barrel is compressed.

After armed needles are formed, they must be tested to determine if they satisfy certain requirements demanded by surgeons. For example, U.S. Pat. No. 3,980,177 discloses a requirement of a surgeon or medical personnel to be able to detach an armed surgical needle from a suture after suturing to avoid the necessity of cutting the suture with scissors. The '177 patent discloses a needle-suture combination having a straight pull-out value of between about three (3) ounces and 26 ounces depending upon the size of the suture. The '177 patent, however, does not disclose a means for testing the armed surgical needle to determine its pull-out value, i.e., the force necessary to detach the needle from the suture.

A conventional method for testing a needle and suture attachment includes a step of manually pulling the suture to a minimum force level. This is typically done by the same operator following a swaging operation. To pull-test the needle-suture attachment, the operator is required to move the needle and suture from a swaging station to a separate pull testing fixture. There are various aspects of this methodology that are not optimal. First, the operator is required to remove the needle-suture assembly from the swaging apparatus and mount it to a pull test station, which takes time. Second, the additional handling of the needle-suture assembly increases the opportunity for the suture to be damaged. Third, the integrity of the needle-suture assembly can be compromised if the suture is pulled for too long (i.e., the suture may start to creep out of the needle receiving hole), which can result in weakened attachment strength.

In spite of the above advances, there remains a need for improved swaging systems that make and test armed surgical needles in more efficient, effective, and reliable manners. In addition, there remains a need for improved manual swaging systems for using fine needles and suture for making armed surgical needles for delicate surgical procedures. There also remains a need for swaging systems that produce armed surgical needles whereby the integrity of the needle and suture attachment meets minimum strength requirements in a consistent and efficient manner.

SUMMARY OF THE INVENTION

In one embodiment, a combined needle swaging and testing system preferably includes a swaging press having a die that may be used for both swaging a needle (i.e., attaching a needle to the end of a suture), and conducting a pull test on the armed surgical needle to assess the needle and suture attachment.

In one embodiment, the combined needle swaging and testing system desirably includes a control system that generates both visual and audible cues to an operator of the swage press during the testing to ensure that the needle and suture attachment is not severely overstressed or held at a high force for an extended period of time that could cause undetected damage to the needle and suture attachment.

In one embodiment, a swage press preferably includes upper and lower presses having respective upper and lower die that are used for a swaging process. In one embodiment, the lower die preferably includes a hinge mechanism disposed within the lower press that is placed horizontally in the lower press and that is orthogonal to the direction of swaging. The hinge mechanism preferably has a bottom plate that is secured on the lower die, which, in turn, is mounted on the frame of the swaging system. The hinge mechanism preferably includes a top plate that is designed and configured to receive the swage tooling. The bottom and top plates are preferably connected on one side with a precision ground rod to form a hinge and the other side of the bottom plate desirably contains a recess that is configured to accommodate a load cell. In one embodiment, during a swaging event, the hinge mechanism holds the bottom plate in place, however, after the swaging event, it serves to measure the pull force applied to a needle and suture attachment, as described herein.

In one embodiment, the swaging tooling that is connected to the top plate of the hinged mechanism desirably has an additional "testing" notch that is larger than the suture diameter, but smaller than the needle diameter. As such, after swaging a needle to a suture, the suture and attached needle may be moved a very small distance away from the location of the swage notch (e.g., 1 mm or less) to nest in the testing notch, and then that suture is pulled until the proximal end of the needle catches in the relatively smaller width testing notch. Since the entire apparatus is connected through a hinge, as the suture is pulled, the weight of the top plate of the hinged mechanism that is translated through the load cell is lessened. This decreasing force (i.e., removal of weight from the load cell) is monitored at a rate of several thousand times per second through a microprocessor that receives load signals from the load cell.

In one embodiment, the output pins of a microprocessor are connected to a light emitting element, such as a red-green-blue (RGB) light emitting diode that can be viewed directly through the stereoscope used by the swaging operator, thus preventing the need for the operator to move his or her head and look away from the work at hand, which minimizes operator fatigue and optimizes output. In one embodiment, other microprocessor output pins may be connected to a buzzer or chime to provide audible signals to the operator. In one embodiment, an operator will receive both visual and auditory signals during the pull test that help the operator to ensure that the proper prescribed force and time duration of the pull test are achieved.

In one preferred embodiment, for an armed surgical needle having a 7-0 suture, the microprocessor will desirably send a green light signal to the operator when a force drop equivalent to >95 grams is detected by the load cell. If a force of between 95 and 115 grams is maintained for a minimum of 0.2 s, then the microprocessor will send signals to turn the light blue and a triple beep will be provided by the buzzer. The operator must then release the force on the suture before the triple beep ceases (at 0.6 s). If the pull force at any time exceeds 115 grams, or if the operator pulls the suture continuously for more than about 0.6 s, then the RGB LED will turn red and a continuous, annoying audible signal will be generated from the buzzer signaling the operator to discard the sample he or she just tested.

In one embodiment, the swaging system disclosed herein blends the capabilities of humans with the capabilities of high speed processors to greatly improve the control, efficiency and reliability of pull tests.

In one embodiment, a system for attaching a needle to a suture preferably includes a top swaging die, a frame, an arm pivotally mounted to the frame, the arm having a proximal end and a distal end, a bottom swaging die mounted on top of the arm, a top swaging die moveably mounted to the frame and aligned with the bottom swaging die, and a load cell mounted to the frame and in contact with the distal end of the arm.

In one embodiment, a method of swaging and pull testing a suture attached to a needle desirably includes swaging a needle to a suture using the above-described system, positioning the armed surgical needle into a testing notch, pulling the suture, and sensing a force change due to pulling the suture.

In one embodiment, the lower swage die preferably includes a testing notch that has an opening larger than the suture diameter but less than that of the swaged needle.

In one embodiment, the needle is left in the lower die after swaging and the suture is pulled perpendicular to the swage die.

In one embodiment, the load cell communicates with a microprocessor.

In one embodiment, the arm rests on the load cell. In one embodiment, the load cell rests on the arm.

In one embodiment, the swaging press may have a foot pedal to interrupt power to the load cell when the pedal is pressed and restore power after a pre-defined period of time following swaging (e.g., 500 ms).

In one embodiment, the swaging system may include audible and/or visual indicators. In one embodiment, the indicator(s) are activated when a change in force (as measured by the load cell) reaches one or more predetermined force levels and/or time periods.

In one embodiment, the visual and audible indicator(s) exhibit different indications (e.g., colors, sounds, vibrations, etc.) based on predetermined force levels and/or time periods.

In one embodiment, the system may include a feedback mechanism designed to increase the force or displacement of swaging during the next swaging event should a needle-suture attachment fail during testing.

In one embodiment, the swaging system may be entirely or partly automated.

In one embodiment, a swaging system for attaching surgical needles to sutures and testing the attachment strength desirably includes a frame, a bottom swaging die mounted on the frame, and a top swaging die mounted on the frame. In one embodiment, the top swaging die is moveable up and down along a swaging axis that is in alignment with the bottom swaging die. In one embodiment, the bottom swaging die includes a hinge mechanism with a bottom plate mounted to the frame and a top plate overlying the bottom plate. In one embodiment, the top and bottom plates are pivotally connected to one another for enabling the top plate to pivot relative to the bottom plate. The bottom swaging die preferably includes a swaging tool mounted on the top plate that extends toward the top swaging die along the swaging axis. In one embodiment, the system includes a load cell disposed between the top and bottom plates for monitoring the load on the top plate.

In one embodiment, the swaging tool desirably includes an upper end having a top surface with a swaging notch for swaging a needle to a suture to form an armed surgical needle, and a testing notch, adjacent the swaging notch, for conducting a pull test on the armed surgical needle. In one embodiment, the swaging and testing notches may extend along respective longitudinal axes that are orthogonal to the swaging axis. In one embodiment, the swaging and testing notches preferably extend along respective longitudinal axes that are parallel with the top surface of the top plate and perpendicular to the swaging axis.

In one embodiment, the swaging notch desirably has a first width and the testing notch has a second width that is smaller than the first width. In one embodiment, a needle components of an armed surgical needle has a diameter that is less than or equal to the first width of the swaging notch and greater than the second width of the testing notch, and the suture component of an armed surgical needle has a diameter that is less than the first width of the swaging notch and the second width of the testing notch. In one embodiment, the first width of the swaging notch is about 8 mil, the second width of the testing notch is about 4 mil, the diameter of the needle is about 7.5-7.8 mil, and the diameter of the suture is about 3.5 mil.

In one embodiment, the swaging system preferably includes a control system having at least one microprocessor in communication with the load cell for receiving load signals measured by the load cell. The microprocessor is preferably adapted for detecting changes in the load signals measured by the load cell.

In one embodiment, the control system desirably includes one or more pull test programs stored therein for conducting pull tests on armed surgical needles. Each pull test program desirably has an acceptable load range having predetermined lower and upper load limits, and an acceptable time range having predetermined lower and upper time limits for the length of a load test.

In one embodiment, a pull test program enables a human to commence a pull test inspection when a load change is detected by the microprocessor. In one embodiment, a pull test program indicates that the tested armed surgical needle is acceptable if the detected load change is between the predetermined lower and upper load limits and the detected time is between the predetermined lower and upper time limits. In one embodiment, the pull test program indicates that the tested armed surgical needle is unacceptable if the detected load change is above the predetermined upper load limit. In one embodiment, the pull test program indicates that the tested armed surgical needle is unacceptable if the detected load change is between the predetermined lower and upper load limits and the detected time is above the predetermined upper time limit.

In one embodiment, during a pull test inspection of an armed surgical needle, the control system preferably generates visible or audible signals that indicate whether the tested armed surgical needle is acceptable or unacceptable. In one embodiment, the control system generates visible green light and an audible beep if the tested armed surgical needle is acceptable and visible red light and an audible buzzer if the tested armed surgical needle is unacceptable.

In one embodiment, a swaging system for attaching surgical needles to sutures and testing the attachment strength of armed surgical needles preferably includes a frame, a bottom swaging die mounted on the frame, and a top swaging die mounted on the frame and being moveable up and down along a swaging axis that is in alignment with the bottom swaging die.

In one embodiment, the bottom swaging die desirably has a hinge mechanism including a bottom plate mounted to the frame, a top plate overlying the bottom plate, whereby the top and bottom plates are pivotally connected to one another for enabling the top plate to pivot relative to the bottom plate, and a swaging tool mounted on the top plate that extends toward the top swaging die along the swaging axis, the swaging tool includes an upper end having a top surface with a swaging notch for swaging a needle to a suture to form an armed surgical needle, and a testing notch, adjacent the swaging notch, for conducting a pull test on the armed surgical needle. In one embodiment, the hinge mechanism preferably includes a load cell disposed between the top and bottom plates for monitoring the load on the top plate.

In one embodiment, the swaging system desirably has a control system with at least one microprocessor in communication with the load cell for receiving load signals generated by the load cell and detecting changes in the load signals. In one embodiment, the control system desirably has one or more pull test programs stored therein for conducting pull tests on armed surgical needles. In one embodiment, each pull test program preferably includes an acceptable load range having predetermined lower and upper load limits, and an acceptable time range having predetermined lower and upper time limits.

In one embodiment, the pull test program enables commencement of a pull test inspection when a load change is detected by at least one microprocessor. In one embodiment, a pull test program indicates that the tested armed surgical needle is acceptable if the detected load change is between the predetermined lower and upper load limits and the detected time is between the predetermined lower and upper time limits. In one embodiment, a pull test program indicates that the tested armed surgical needle is unacceptable if the detected load change is above the predetermined upper load limit. In one embodiment, a pull test program indicates that the tested armed surgical needle is unacceptable if the detected load change is between the predetermined lower and upper load limits and the detected time is above the predetermined upper time limit.

In one embodiment, during a pull test inspection of an armed surgical needle, the control system is configured to generate visible or audible signals that indicate whether the tested armed surgical needle is acceptable or unacceptable. In one embodiment, the control system generates visible green light and a first audible sound if the tested armed surgical needle is acceptable and visible red light and a second audible sound, different from the first audible sound, if the tested armed surgical needle is unacceptable.

In one embodiment, a stereoscope is mounted on the frame for viewing the swaging and inspection notches at the top surface of the swaging tool. In one embodiment, the stereoscope desirably has at least one light emitting diode for generating visible light, such as green visible light and red visible light for indicating the status of the attachment test.

In one embodiment, the hinge mechanism preferably includes a pin interconnecting adjacent sides of the top and bottom plates for pivotally connecting the top and bottom plates. In one embodiment, the bottom plate preferably has a guard located on a side of the bottom plate that is opposite the pin. In one embodiment, the guard has an upper end that extends above the top surface of the top plate for preventing an operator from inadvertently contacting the top surface of the top plate.

In one embodiment, the bottom plate of the hinge mechanism has a recess and the load cell is disposed within the recess. In one embodiment, the load cell has an adjustable set screw projecting from an upper end of the load cell, and the top plate has a set screw opening accessible at the top surface of the top plate for accessing the set screw of the load cell.

In one embodiment, a swaging system for attaching surgical needles to sutures and testing the attachment strength desirably includes a frame, a bottom swaging die mounted on the frame, and a top swaging die mounted on the frame and being moveable up and down along a swaging axis that is in alignment with the bottom swaging die.

In one embodiment, the bottom swaging die preferably has a hinge mechanism including a bottom plate mounted to the frame, a top plate overlying the bottom plate, whereby the top and bottom plates are pivotally connected to one another for enabling the top plate to pivot relative to the bottom plate, and a swaging tool mounted on the top plate that extends toward the top swaging die along the swaging axis. In one embodiment, the swaging tool desirably has an upper end having a top surface with a swaging notch accessible at the top surface for swaging a needle to a suture to form an armed surgical needle, and a testing notch accessible at the top surface, adjacent the swaging notch, for conducting a pull test on the armed surgical needle. In one embodiment, the swaging and testing notches preferably extend along respective longitudinal axes that are orthogonal to the swaging axis. In one embodiment, a load cell is preferably disposed between the top and bottom plates for monitoring the load on the top plate.

These and other preferred embodiments of the present invention will be described in more detail below.

DETAILED DESCRIPTION OF PREFERRED EMBODIMENTS

Figure 1:
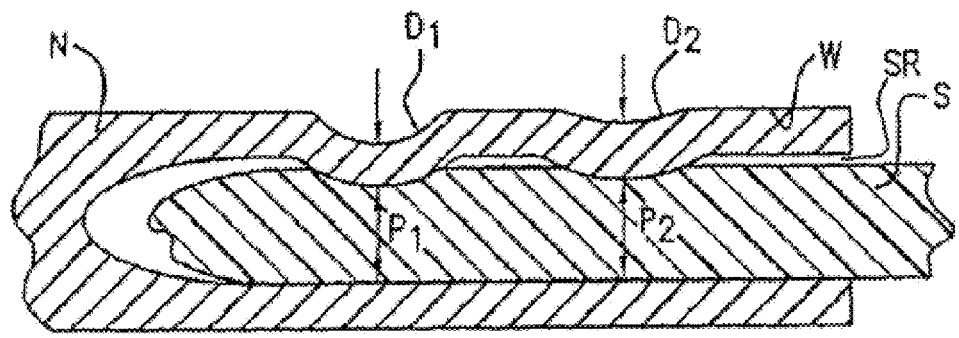
FIG. 1 shows a conventional method of swaging a needle to a suture.
Figure 2:
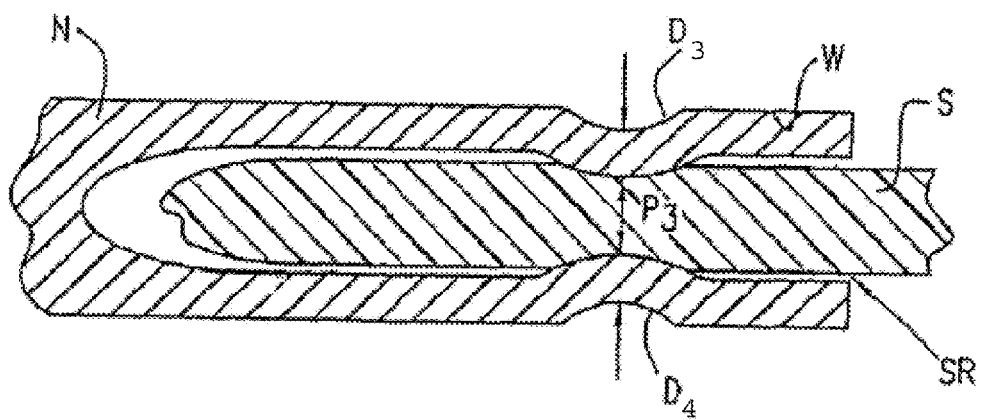
FIG. 2 shows a second conventional method of swaging a suture to a needle.
Figure 3:
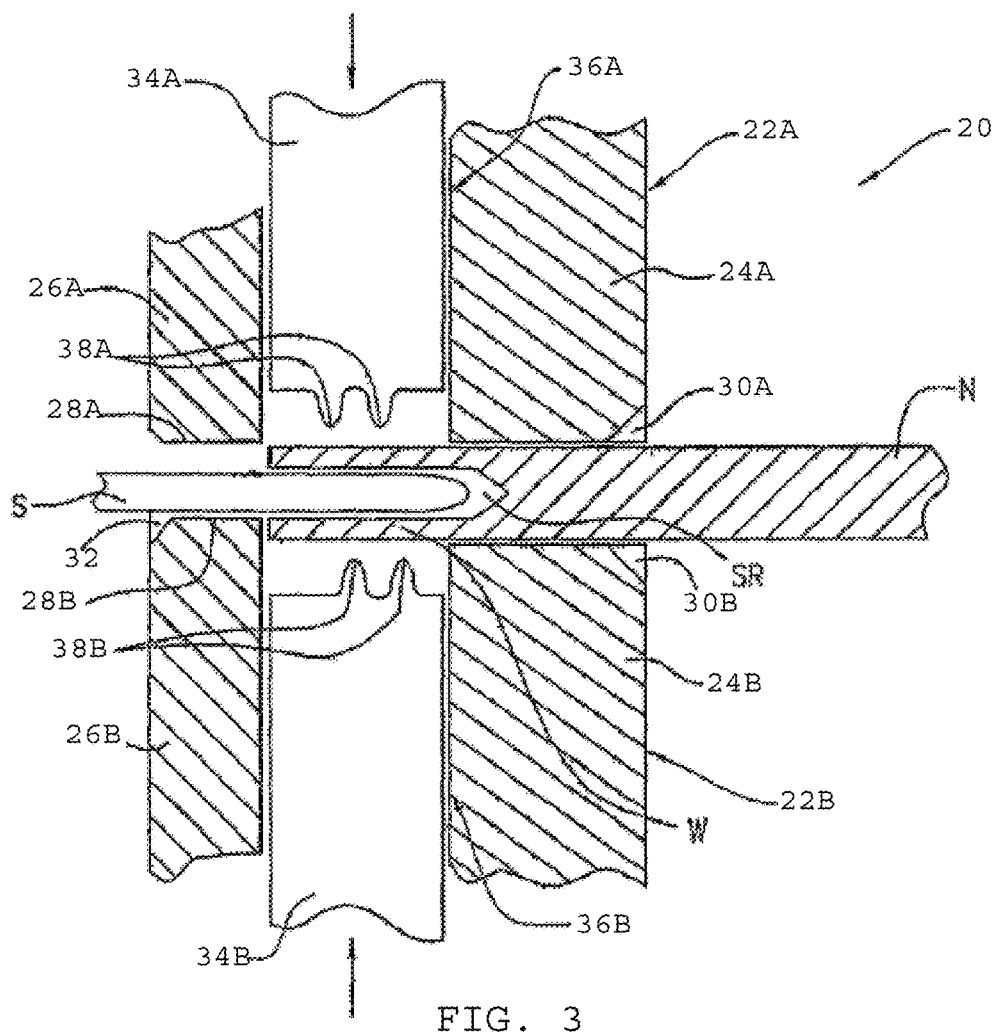
FIG. 3 shows a prior art needle swaging assembly having first and second swage dies that converge to attach a needle to a suture.
Figure 4:
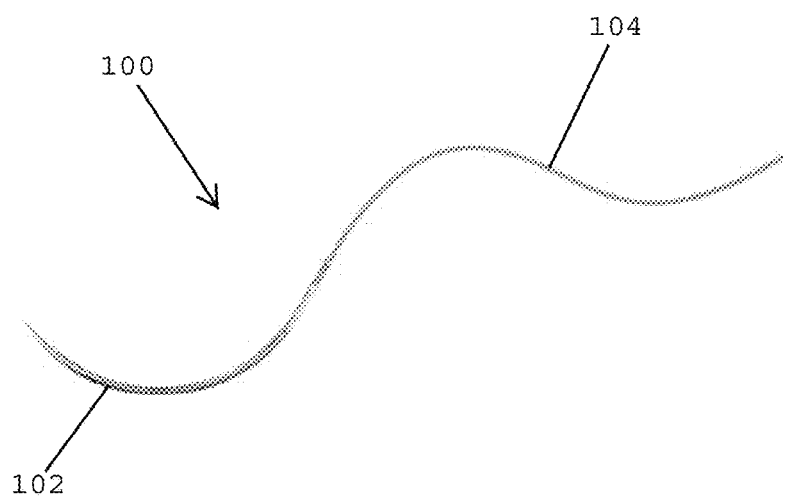
FIG. 4 shows an armed surgical needle including a needle and a suture, in accordance with one embodiment of the present patent application.

Referring to FIG. 4, in one embodiment, an armed surgical needle 100 preferably includes a surgical needle 102 that is secured to the end of a suture 104. In one embodiment, the needle 102 is made of a broad variety of rugged materials including metal alloys such as stainless steel, 4310 SS, nickel-titanium (NiTi) SS and 420 SS, or advanced alloys, such as, tungsten-rhenium (W—Re) alloys or similar refractory alloys. In one embodiment, the needle 102 is made of a tungsten-rhenium alloy that is sold under the trademark EVERPOINT® by Ethicon, Inc. of Somerville, N.J.

In one embodiment the suture material may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture material may include combinations of both absorbable and non-absorbable materials. In addition, metals may be suitable for certain applications, such as instances where specific strength, electrical conductivity, or corrosion resistance is necessary. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like. In one embodiment, the needle 102 is coated with a silicon coating. In one embodiment, the suture 104 is a polypropylene suture sold under the trademark PROLENE® by Ethicon, Inc of Somerville, N.J.

Figure 5A:
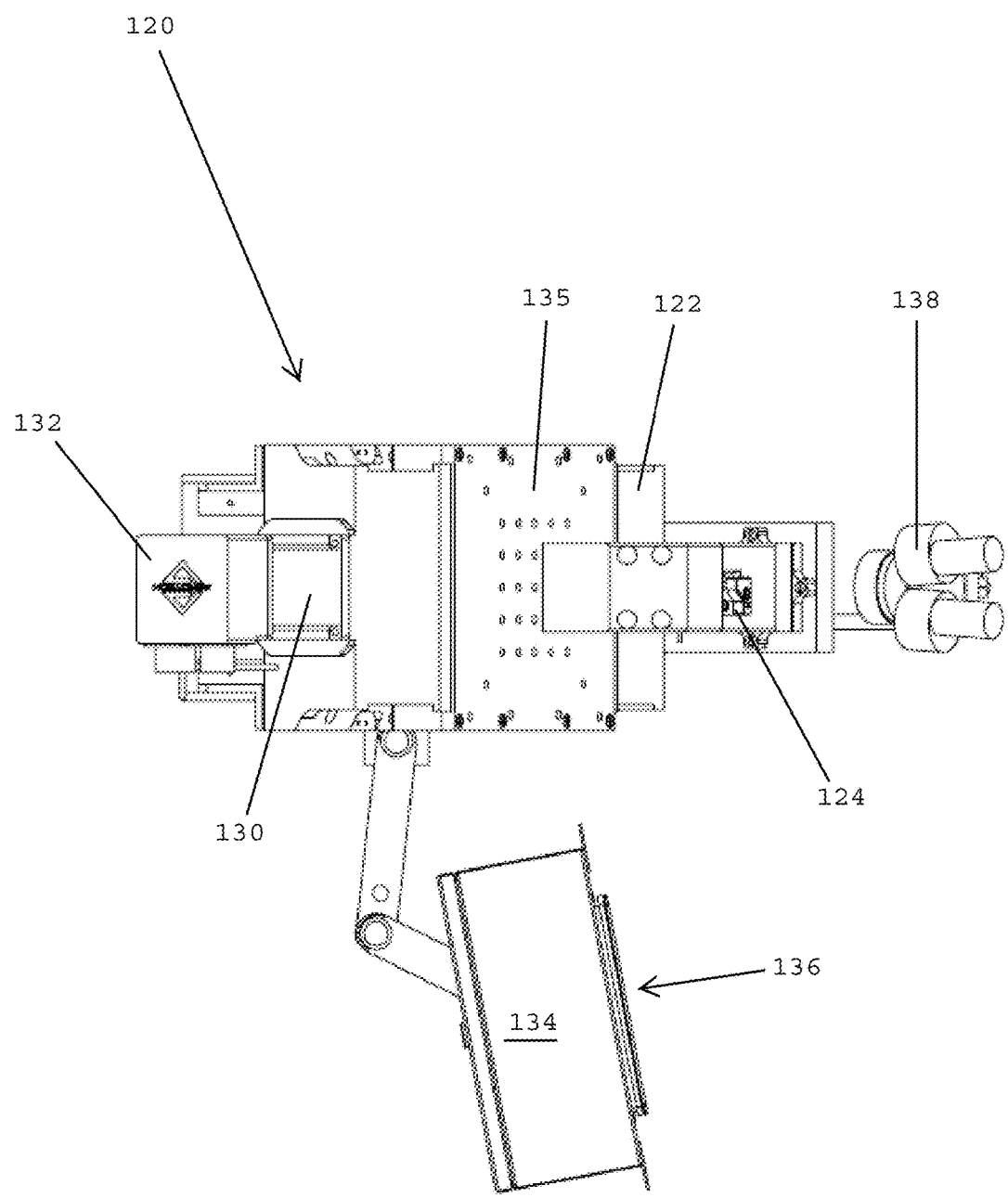
FIGS. 5A-5C show a swaging system for attaching surgical needles to sutures, in accordance with one embodiment of the present patent application.
Figure 5B:
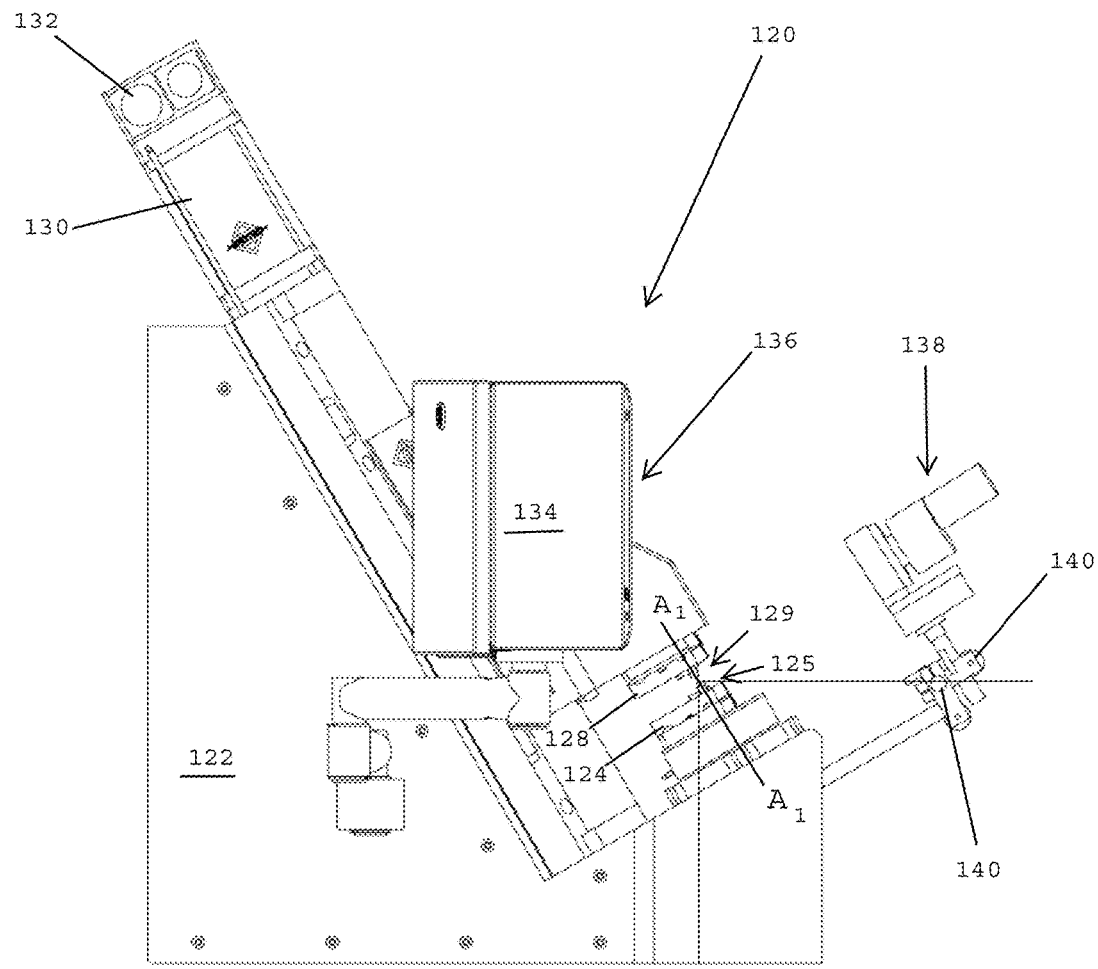
Figure 5C:
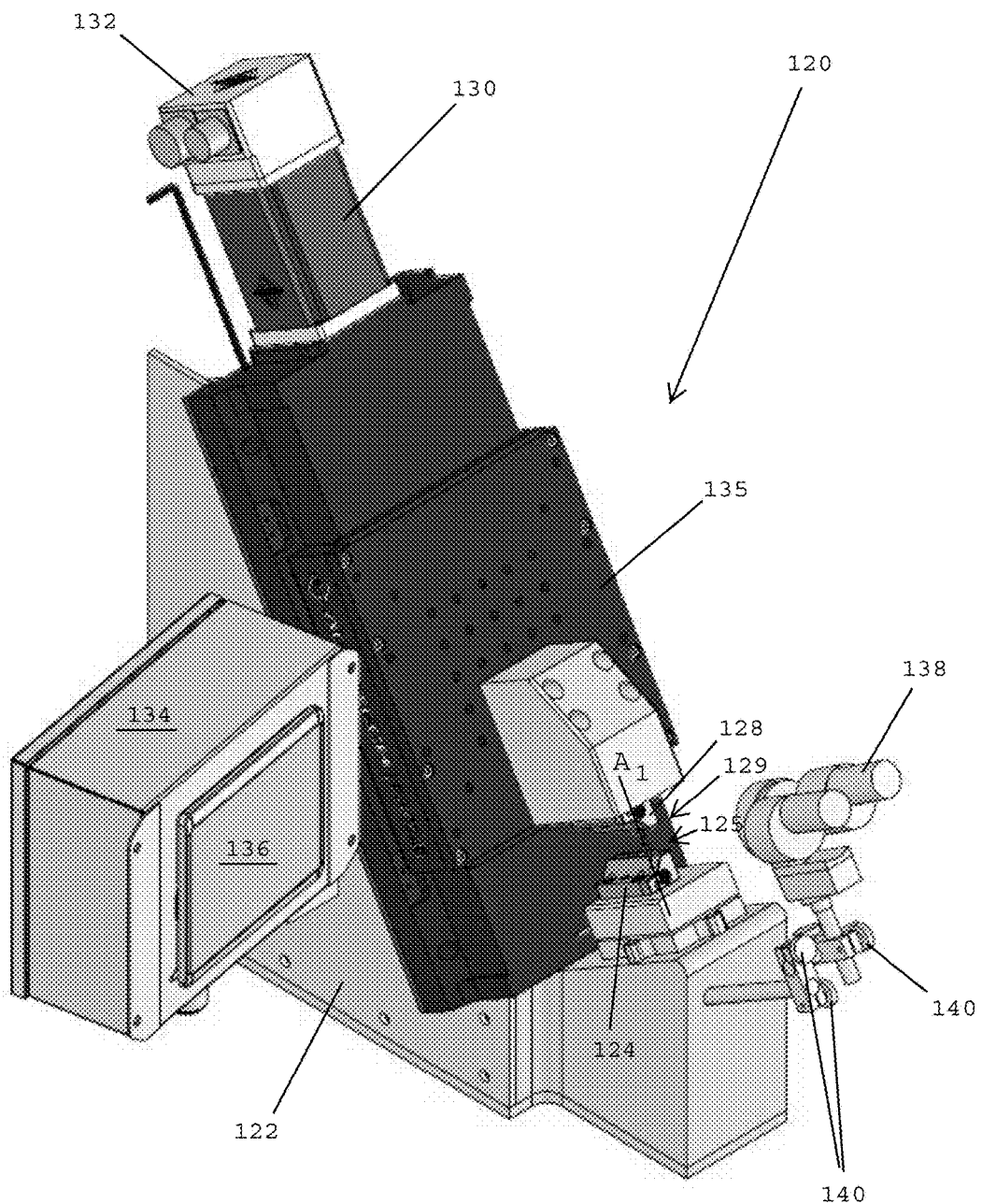

Referring to FIGS. 5A-5C, in one embodiment, a swaging press 120 for making armed surgical needles preferably includes a frame 122 having a bottom die holder block 124 with a bottom swaging die 125 mounted thereon, and a top die block holder 128 having a top swaging die 129 that is adapted to move up and down along a swaging axis $A_1$ that is aligned with the bottom swaging die 125. In one embodiment, the top swaging die 129 is mounted on a precision slide 135 that is configured to slide up and down on the frame 122. The swaging press 120 desirably includes a servomotor 130 that is activated for moving the precision slide 135, the top die block holder 128, and the top swaging die 129 up and down along the swaging axis $A_1$ relative to the bottom swaging die 125. The swaging press system 120 preferably includes a power connection 132 for the servomotor 130. The power connection 132 may house an encoder that provides position feedback information for the top swaging die 129.

In one embodiment, the swaging system 120 preferably includes a human machine interface (HMI) 134 that is connected to and/or positioned adjacent the frame 122. In one embodiment, the HMI 134 desirably has an LCD display 136 that enables an operator to interface with the HMI 134 for selecting a particular swaging program and/or monitoring a swaging and testing operation. In one embodiment, the HMI 134 preferably includes a control system having one or more microprocessors, memory devices, and programs for operating the swaging system 120. In one embodiment, the microprocessor contained within the HMI 134 desirably has numerous programs and/or subroutines loaded therein that may be selected by an operator so that the swaging system 120 may be utilized for making a wide range of armed surgical needles having needles with a range of different sizes and suture material having a range of different sizes.

In one embodiment, the swaging system 120 desirably includes a stereoscope 138 that is mounted to the frame 122. The stereoscope 138 is preferably aimed at the lower die 125 for using during swaging and testing operations, as will be described in more detail herein. The stereoscope 138 desirably includes optics that provide for a magnified view of the needles, suture material, and opposing dies during swaging and testing operations. In one embodiment, the stereoscope 138 may include tightening knobs 140 adjusting and locking the position of the stereoscope optics relative to the opposing dies, and the swaging and testing locations on the dies, and magnification adjustment knobs for adjusting magnification levels.

In one embodiment, the stereoscope 138 may include one or more light generating elements, such as red-green-blue (RGB) light emitting diodes, that may be viewed directly through the stereoscope used by the swaging operator, thus eliminating the need for the operator to move his or her head and look away from the work at hand. In one embodiment, the RGB diode is desirably mounted on either the top or bottom die holder blocks within the field of view of the stereoscope. This benefit is related to minimizing operator fatigue and optimizing output. In one embodiment, microprocessor output pins are connected to an audible signal generator, such as a beeper or buzzer, to provide audible signals or sounds for an operator of the swaging system. As such, an operator may receive both visual and auditory signals during testing that help the operator to insure that the proper prescribed force and duration of pull tests have been achieved.

In one embodiment, the red-green-blue light emitting diodes within the stereoscope 138 are in communication with the control system within the HMI 134 (FIG. 5C).

Figure 6A:
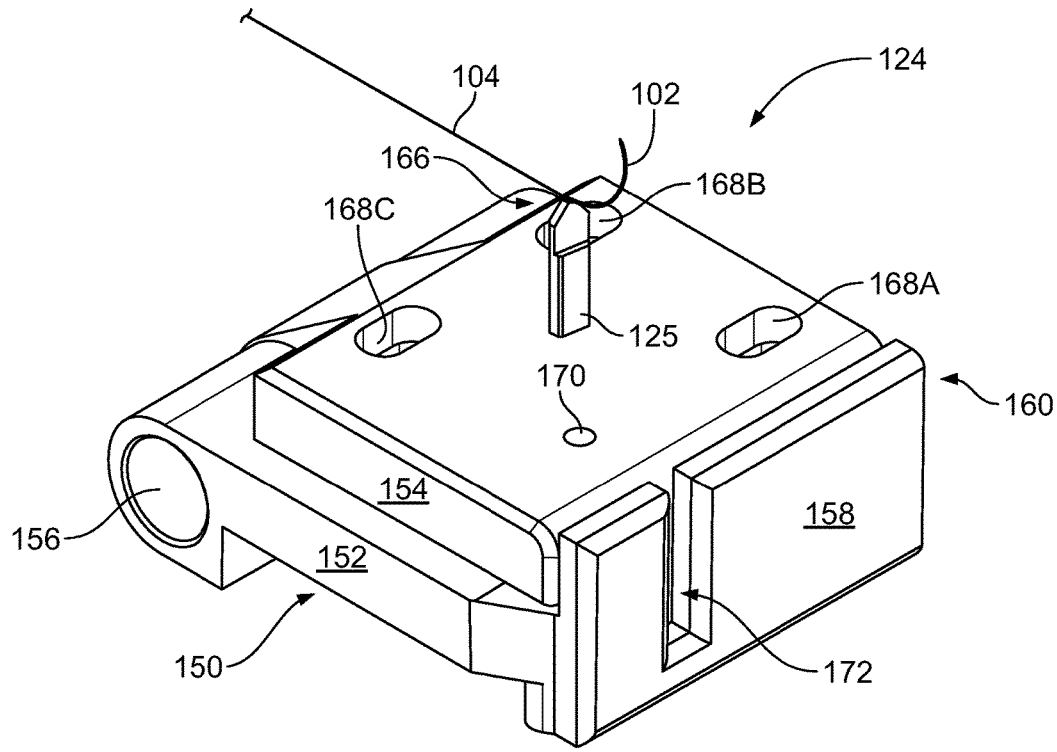
FIG. 6A shows a perspective view of a hinged assembly of a lower swage die, in accordance with one embodiment of the present patent application.
Figure 6B:
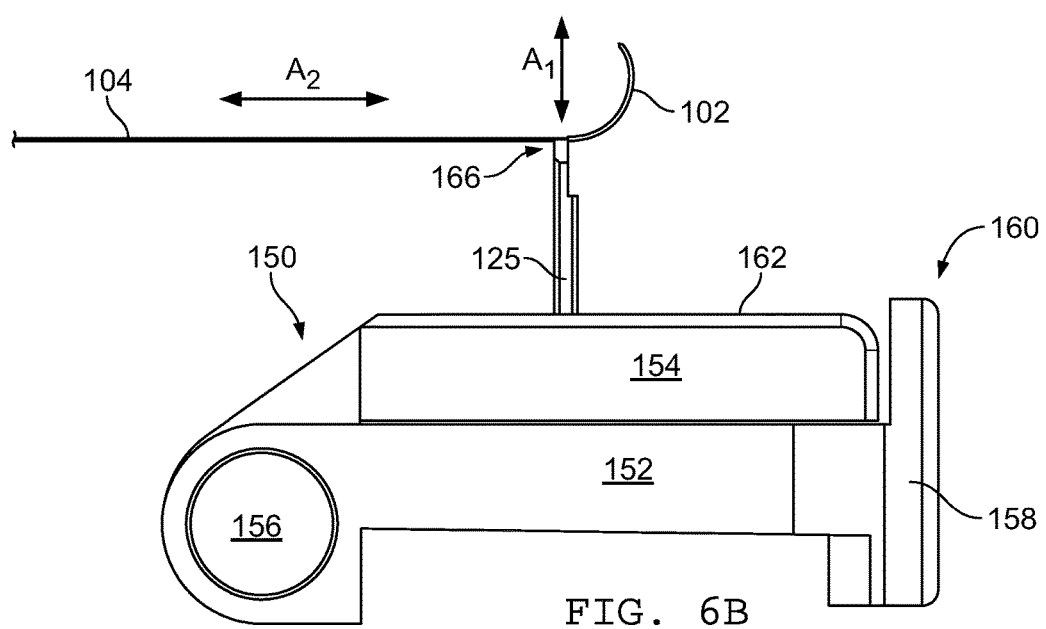
FIG. 6B shows a side elevation view of the hinged assembly shown in FIG. 6A.

Referring to FIGS. 6A and 6B, in one embodiment, the swaging system preferably includes a hinge mechanism 150 that is coupled with the lower die 125 (FIGS. 5A-5C). In one embodiment, the hinge mechanism 150 is desirably placed horizontally in the lower die and orthogonal to the direction of the swaging axis $A_1$ (FIGS. 5B, 5C and 6B). In one embodiment, the hinge mechanism 150 desirably includes a bottom plate 152 and a top plate 154 that serves as a mounting platform for the lower swaging die and that overlies the bottom plate 152. The hinge mechanism 150 preferably includes a hinge 156 that enables the top plate 154 to pivot about the hinge 156 relative to the bottom plate 152. In one embodiment, the hinge mechanism 150 may include bearings or bushings in contact with the hinge 156 for minimizing friction as the top plate 154 pivots and moves relative to the bottom plate 152.

In one embodiment, the hinge mechanism 150 preferably includes a guard 158 that is secured to an end of the bottom plate 152 or made integral with it on a side of the bottom plate that is opposite the hinge 156. In one embodiment, the guard 158 has an upper end 160 that projects above a top surface 162 of the top plate 154 to prevent an operator from inadvertently bumping into and/or contacting the top half 154 thereby sending erroneous signals through the load cell to the microprocessor.

Referring to FIG. 6B, in one embodiment, the hinge mechanism 150 preferably includes a swaging tool 125 or bottom swaging die projecting upwardly from the top surface 162 of the top plate 154. In one embodiment, the swaging tool 125 desirably has an upper end 166 that is adapted to receive a needle 102 and a suture 104 for attaching the needle to the suture. In one embodiment, the upper end 166 of the swaging tool 125 has a first notch for swaging the needle 102 to the suture 104 (i.e., the swaging notch), and a second notch for inspecting the attachment of the needle 102 to the suture 104 (i.e., the inspection notch).

Referring to FIG. 6A, in one embodiment, the top plate 154 of the hinge mechanism 124 desirably includes openings 168A-168C that are utilized for securing a die support plate over the top surface 162 of the top plate 154 for providing support for the base of the swaging tool 125 projecting from the top surface of the top plate. In one embodiment, the top plate 154 also preferably includes a set-screw opening 170 formed in the top surface 162 of the top plate that provides access to a set screw on a load cell disposed within the bottom plate 152, as will be described in more detail herein.

In one embodiment, the guard 158 desirably has an opening 172 formed therein that enables conductive elements, conductive conduits, and/or conductive leads to pass therethrough for interconnecting the load cell of the hinge mechanism with a microprocessor and/or system controller.

Figure 7:
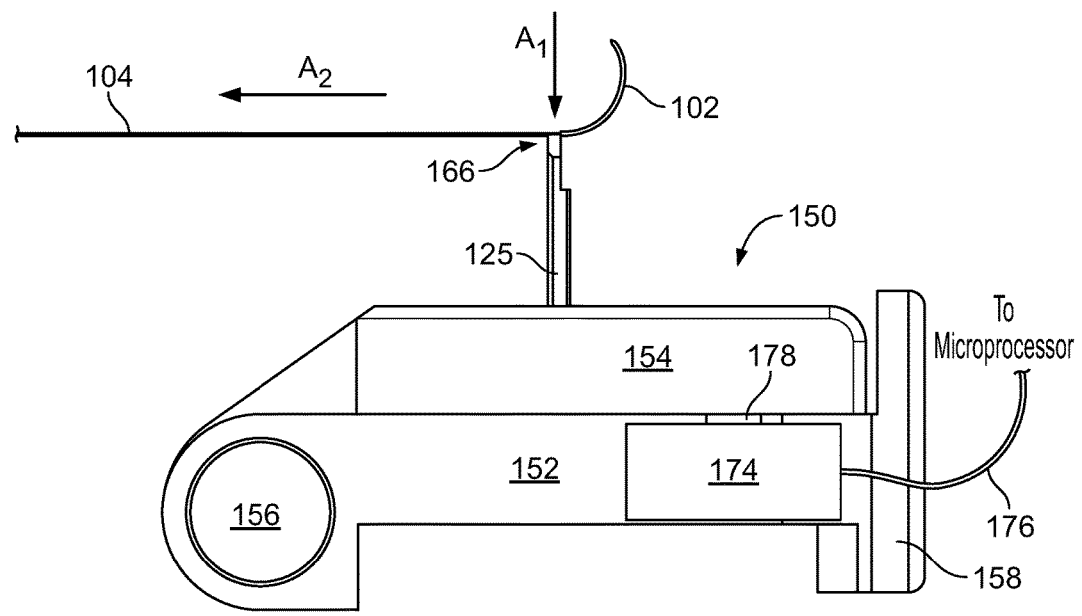
FIG. 7 shows a partial cross sectional view of the hinged assembly shown in FIG. 6B including a swaging tool, and a load cell disposed between top and bottom plates of the hinged assembly.

Referring to FIG. 7, in one embodiment, the hinge mechanism 150 preferably includes a load cell 174 disposed in the bottom plate 152 of the hinge mechanism, which, in turn, is mounted to the lower die holder block 124 or directly to the frame 122 of the press (FIG. 5C). The load cell 174 is preferably coupled with a conductive lead 176 that passes through the opening 172 (FIG. 6A) of the guard 158. The conductive lead 176 is desirably interconnected with a microprocessor and/or a system controller for communicating with the load cell 174. In one embodiment, the load cell 174 preferably has an adjustable set screw 178 that is in alignment with the set screw opening 170 (FIG. 6A) accessible at the top surface 162 of the top plate 154.

In one embodiment, the load cell 174 is a transducer that is used to create an electrical signal whose magnitude is directly proportional to the force being measured. The load cell may be a piezoelectric cell, a strain gauge load cell and/or combinations thereof.

During a swaging process, the hinge mechanism 150 holds the swaging tool 125 in place, however, directly after swaging, the hinge mechanism is configured to measure the pull force exerted upon an armed surgical needle. In one embodiment, in addition to a swaging notch, the upper end 166 of the swaging tool 125 also has a testing notch adjacent the swaging notch that is larger than the diameter of the suture 104 but smaller than the diameter of the needle 102. In this way, after swaging, the suture 104 may be moved a very small distance away from the swaging notch location (e.g. 1 millimeter or less) to the testing notch location.

For testing the armed surgical needle, the suture 104 is pulled in the direction designated $A_2$ in FIG. 7 until the proximal end of the needle 102 catches the testing notch. Axis $A_1$ shows the swaging direction of motion and the direction of gravity. Axis $A_2$ shows the direction that the suture 104 is pulled when the suture (attached to the needle 102) is positioned within the testing notch and the proximal end of the needle 102 engages an end of the relatively smaller diameter testing notch. Since the top plate 154 is connected to the hinge mechanism 150 via the hinge 156, as the suture 104 is pulled in the direction designated $A_2$, the weight of the top plate 154 that is translated through the load cell 174 is lessened. This decreasing load (i.e. removal of weight from the load cell 174) is monitored at a rate of several thousand times per second through a microprocessor in the control system that receives the signals from the load cell.

Figure 8A:
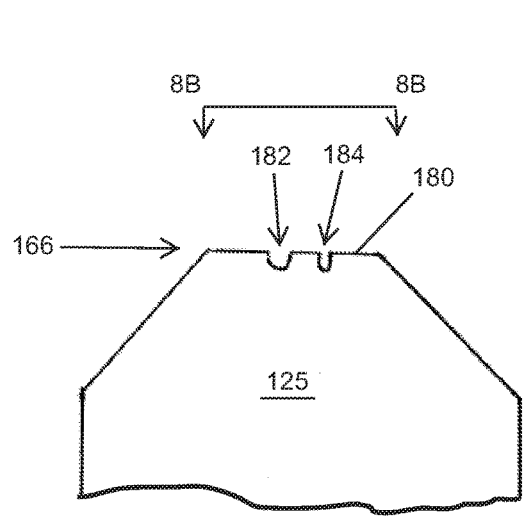
FIGS. 8A and 8B show an upper end of the swaging tool shown in FIG. 7 including a swaging notch and a testing notch, in accordance with one embodiment of the present patent application.
Figure 8B:
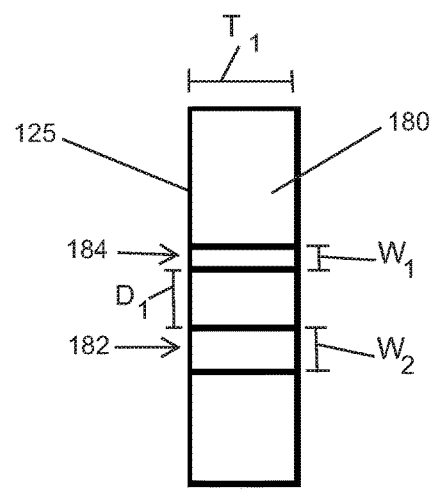

Referring to FIGS. 8A and 8B, in one embodiment, the swaging tool 125 preferably has an upper end 166 with a top surface 180 that is generally parallel with the top surface 162 of the top plate 154 of the hinge mechanism 150 (FIG. 7). In one embodiment, the swaging tool preferably includes a swaging notch 182 that is adapted to receive a needle and a suture during a swaging operation, and an adjacent inspection notch 184 that is utilized for inspecting an armed surgical needle after the needle has been attached to an end of a suture. The swaging notch 182 and the inspection notch 184 desirably extend across the thickness $T_1$ of the top surface 180. In one embodiment, the swaging notch 182 extends across the thickness of the swaging tool and has a width $W_2$ of about 8 mil, and the inspection notch 184 also extends across the thickness of the swaging tool and has a width $W_3$ of about 4 mil. In one embodiment, the distance between the swaging notch 182 and the testing notch 184, designated $D_5$, is preferably about 1 millimeter or less.

In one embodiment, the surgical needle 102 has an outer diameter of about 7.8 mil, which enables the needle to be positioned within the swaging notch 182, but not fit into the adjacent testing notch 184. The suture preferably has a diameter of 3.5 mils so that it may disposed within both the swaging notch 182 and the testing notch 184. Due to the larger relative diameter of the needle vis-a-vis the testing notch 184, the suture may pass through the testing notch 184, but the larger diameter needle may not pass through the testing notch 184, which enables the pull test to be conducted using the hinge mechanism 150 (FIG. 7).

FIGS. 9A-9E show an armed surgical needle including a needle 102 and a suture 104 disposed within the testing notch 184 formed in the top surface 180 of the upper end 166 of the swaging tool 125. The surgical needle 102 has a larger diameter than the width of the testing notch 184 so that only the relatively smaller diameter suture 104 may pass through the testing notch 184 while the larger diameter needle 102 is caught at an end of the testing notch. The swaging notch 182 is disposed adjacent the testing notch. The proximal end 105 of the needle 102 has a diameter that is larger than the width of the testing notch 184 so that only the suture 104 may pass through the testing notch 184 while the larger diameter needle 102 is caught at the end of the testing notch 184.

Figure 10:
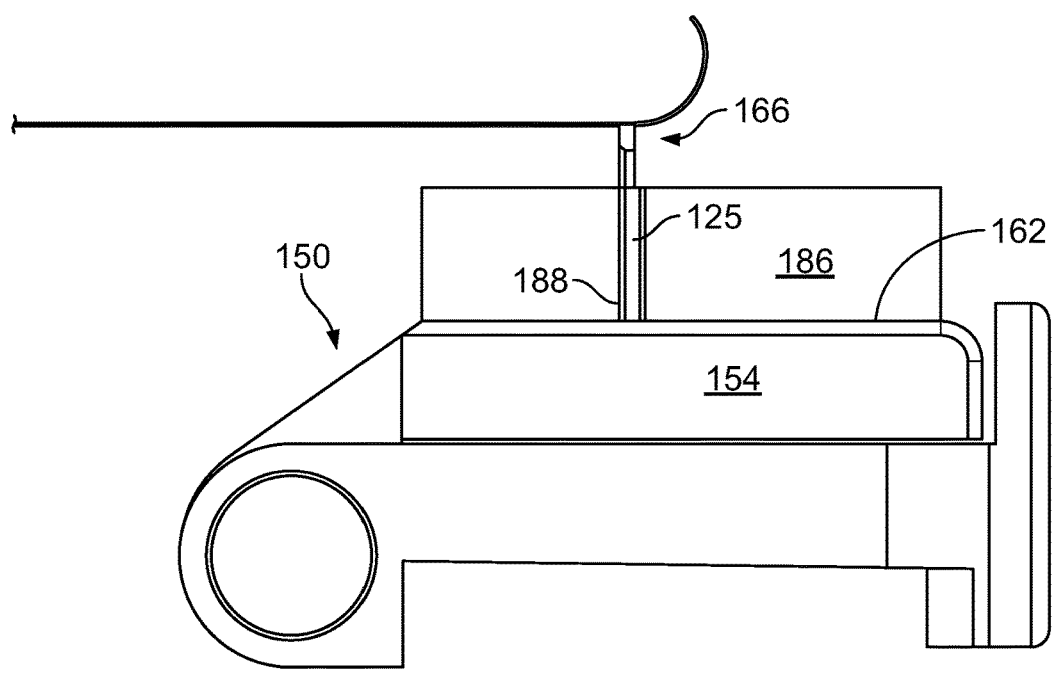
FIG. 10 shows a hinged assembly of a lower die of a swaging system, in accordance with one embodiment of the present patent application.

Referring to FIG. 10, in one embodiment, the hinge mechanism 150 desirably includes a swaging tool support plate 186 that is positioned over the top surface 162 of the top plate 154. In one embodiment, the swaging tool support plate may include projections that are inserted into the swaging tool support plate openings 168A-168C (FIG. 6A). In one embodiment, the swaging tool support plate 186 includes an opening 188 that enables the swaging tool 125 to pass therethrough with the upper end 166 of the swaging tool 125 projecting above the swaging tool support plate 186 to be accessible for swaging and testing operations. The swaging tool support plate 186 preferably supports and maintains the integrity of the swaging tool 125 during swaging and testing operations.

Figure 11:
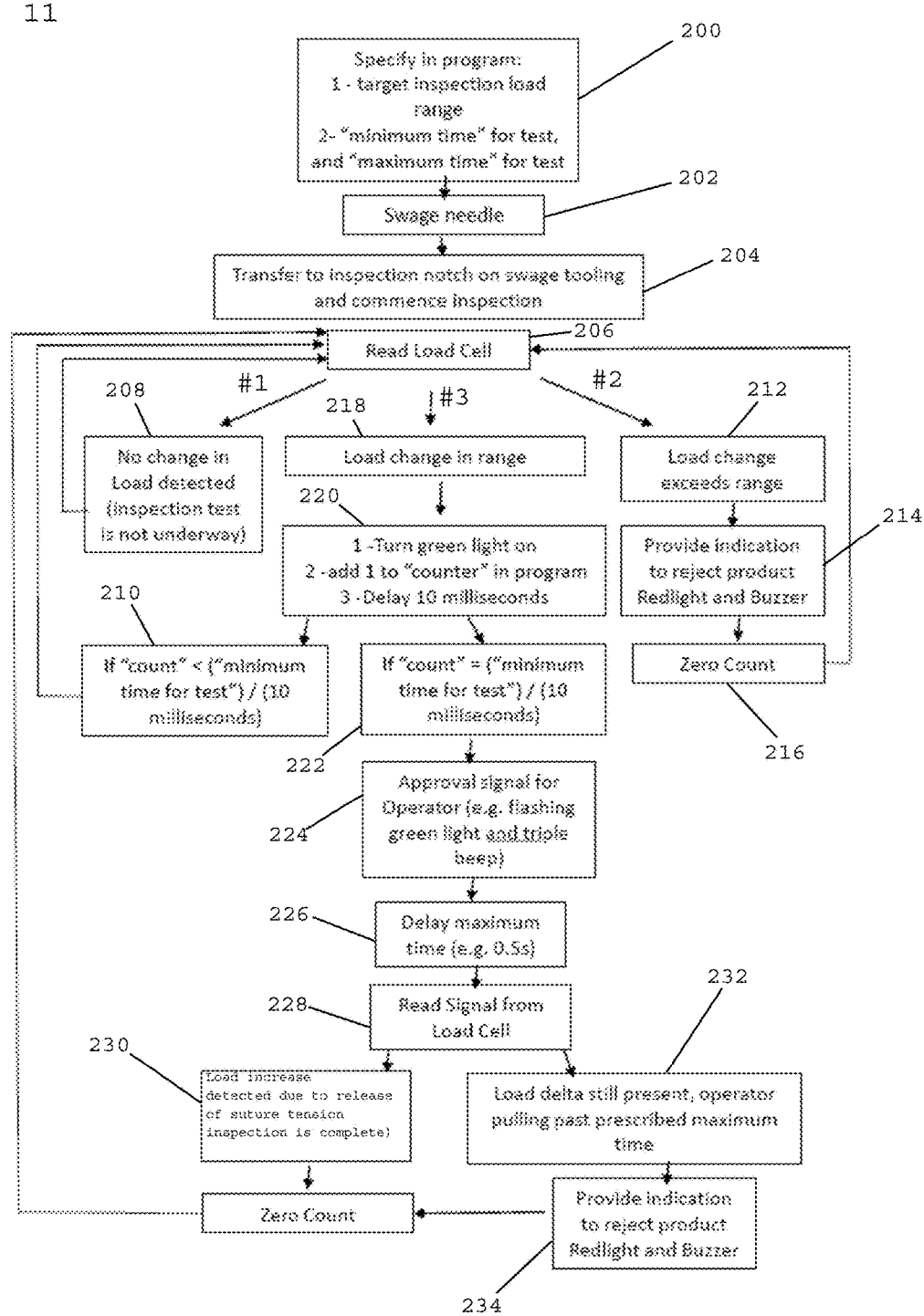
FIG. 11 shows a flow chart upon which a computer operated program is based for swaging and inspecting an armed surgical needle, in accordance with one embodiment of the present patent application.

Referring to FIGS. 5C and 11, in one embodiment, the microprocessor preferably contains one or more swaging and testing programs stored therein. In one embodiment, the swaging system may be utilized to swage and test needles and sutures having different dimensions, sizes, properties and/or configurations. In one embodiment, an operator preferably interacts with an LCD touch screen of the HMI for selecting a particular program for utilization. The program that is utilized may change depending upon the sizes of the needles and sutures being used to form armed surgical needles. The operating programs are preferably stored in one or more microprocessors and/or memory devices. In one embodiment, an operator may modify the load and time parameters of a pull test by inputting data or manipulating controllers and actuators.

A plurality of different swaging and pull test programs may be loaded into a swaging system. An operator preferably selects one swaging and pull test program for operating the swaging system. Referring to FIG. 11, in one embodiment, a pull test program desirably includes a first stage 200 during which an operator specifies or selects a target inspection load range having a lower and upper load limit, and a time limit having a minimum time for conducting the pull test and a maximum time for conducting the pull test. In one embodiment, a target inspection load range may be between about 95-105 grams. In one embodiment, a minimum time for conducting a pull test may be about 0.1 seconds and a maximum time for conducting a pull test may be about 0.5 seconds. In a more preferred embodiment, the minimum time and maximum time range is between 0.2 seconds-0.5 seconds. In one embodiment, it may be important to establish parameters for the target inspection load and the minimum time and maximum time for testing. If too much load is applied to the suture when testing the attachment of the needle to the suture, the attachment may be weakened or damaged. Similarly, if a load is applied to the suture for longer than the maximum time limit, the suture may begin to creep out of its attachment to the needle. Thus, in one embodiment, it may be important to establish testing ranges for both the amount of load applied to the arm surgical needle and the amount of time that suture is pulled after being attached to the surgical needle.

Figure 9A:
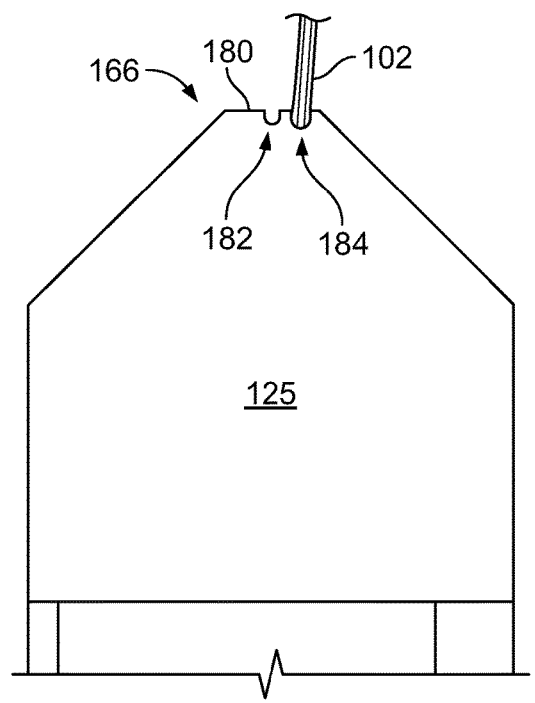
FIGS. 9A-9E show a method of testing an armed surgical needle using the swage tool shown in FIGS. 7, 8A, and 8B, in accordance with one embodiment of the present patent application.
Figure 9B:
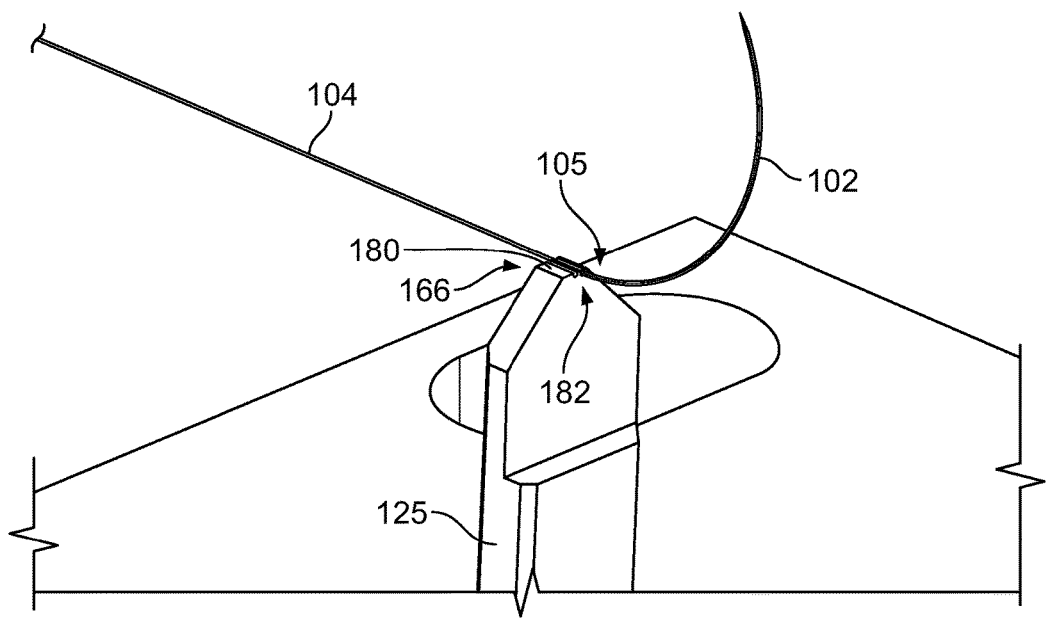
Figure 9C:
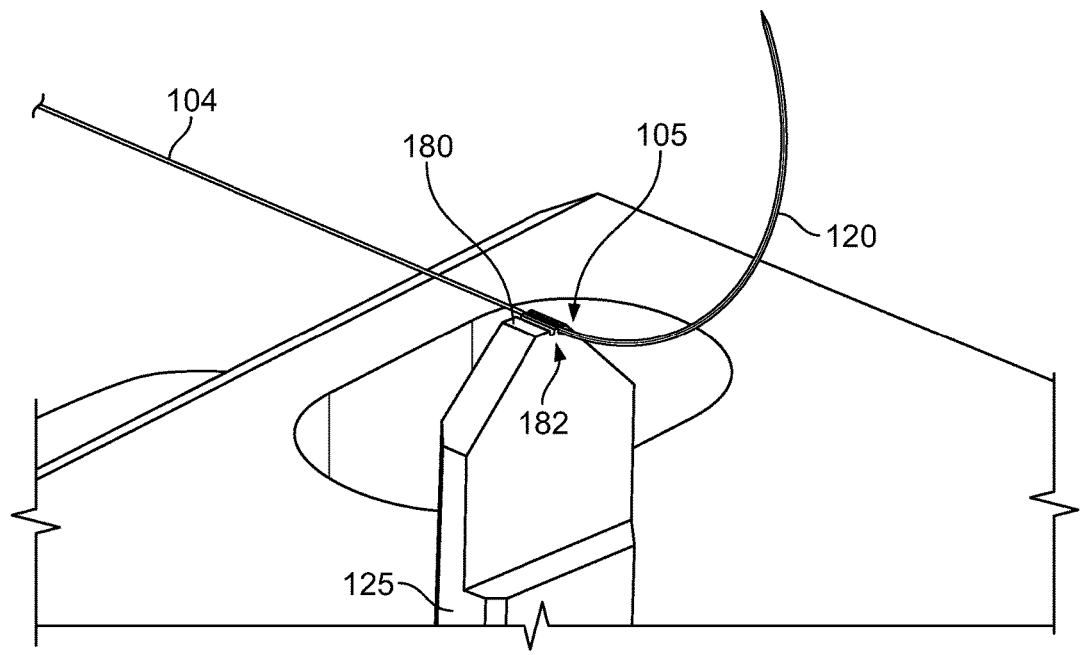
Figure 9D:
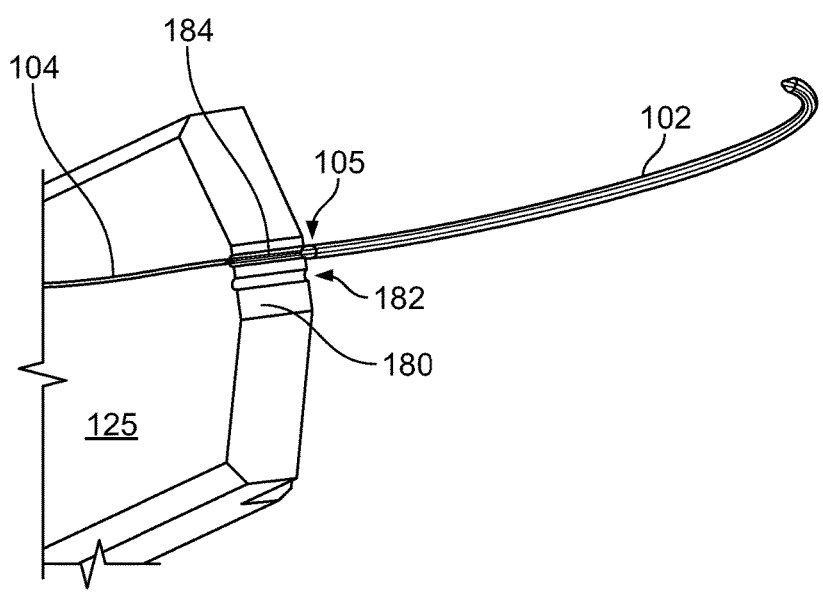
Figure 9E:
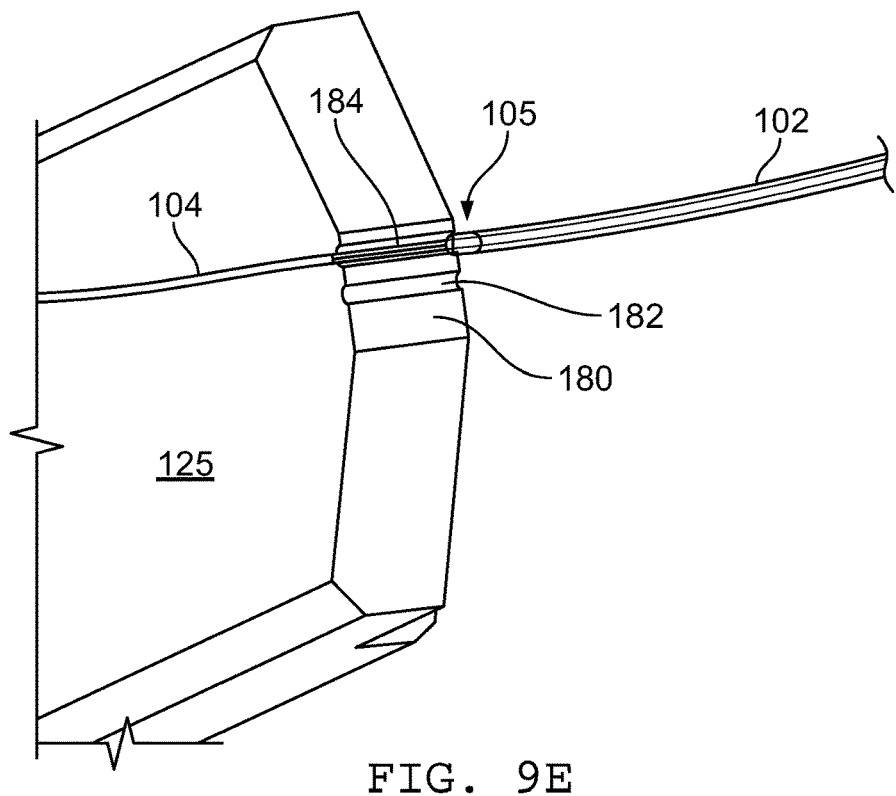

At the next stage designated 202, an operator may depress a foot pedal for closing the upper and lower dies and swaging a needle to a suture. In one embodiment, during stage 202, the needle and the suture are positioned within the swaging notch 182 of the swaging tool 125 (FIGS. 9A-9E). After the upper and lower dies have closed for swaging the needle to the suture, the upper and lower dies open so that the armed surgical needle may be transferred from the swaging notch to the testing notch 184 (FIG. 9D).

Referring to FIG. 11, in one embodiment, at the stage of the program designated 204, the armed surgical needle including the needle secured to the end of the suture is transferred from the swaging notch 182 to the inspection notch 184 (FIG. 9D). The suture 104 may then be pulled in the direction designated $A_2$ in FIG. 7 to commence a pull test. As the suture 104 is pulled to the left in FIG. 7, the top plate 154 of the hinge mechanism 150 is moved away from the bottom plate 152 so that the amount of load applied by the top plate to the load cell 174 is reduced. At the stage of the program designated 206, the load cell reading is transmitted to the microprocessor. In one embodiment, another load reading is taken and transmitted to the microprocessor every 10 milliseconds. Thus, in one embodiment, to reach the minimum time for conducting a single pull test, at least 20 load cell readings are transmitted from the load cell to the microprocessor. If a maximum time of 0.5 seconds is used for obtaining load signals, at least 50 load cell readings are transmitted to the microprocessor. The microprocessor preferably analyzes the load signal data to determine if the load has changed, how much the load has changed, if the measured load change exceeds a predetermined load limit, and the time duration of a pull test.

The flow chart disclosed in FIG. 11 discloses various methodologies and protocols for conducting pull test on armed surgical needles. In a first scenario designated #1, a pull test is commenced. At the stage of the program designated 208, no change in load is detected so the control system determines that a pull test has not yet commenced. The control system continues to conduct a load reading every 10 milliseconds until it detects a change in load, whereupon the control system determines that the pull test has begun and the control system continues the pull test.

In a scenario designated #2, at stage 212, the microprocessor receives a reading from the load cell that the load change is greater than the upper end of the target inspection load range. In one embodiment, the system controller determines that the load change has been exceeded if the measured load is greater than or equal to 105.1 grams. If the load is exceeded, at stage 214, the microprocessor sends signals to generate a red light within the stereoscope and an audible buzzer sound that indicates that the armed surgical needle is defective and should be discarded. At stage 216, after the rejection signals have been transmitted, the control system returns to a zero count.

The scenario designated #3 shows an operational protocol wherein the armed surgical needle is maintained within the target inspection load range and within the minimum/maximum time range for conducting a pull test. At the stage of the program designated 218, the load change is determined to be within the range of 95-15 grams. At stage 220, if the microprocessor determines that the load change is within an acceptable range, the microprocessor generates a green light within the stereoscope or within the field of view of the stereoscope and begins to calculate the length of the test. The microprocessor is preferably adapted to obtain a load cell reading every 10 milliseconds.

At stage 210, if the minimum time for conducting a test has not been reached, the system continues to collect load readings until the minimum time for conducting a pull test has been reached. In one embodiment, the pull test must be conducted for at least 0.1 seconds and more preferably about 0.2 seconds, and the duration of a pull test should not exceed 0.5 seconds.

At stage 222, the microprocessor analyzes if the minimum time for conducting a test has been attained. If not, then the microprocessor continues to collect load cell readings until the minimum time of 0.2 seconds has been reached.

At stage 224, if the target load has been maintained within the acceptable range for at least the minimum period of time, the microprocessor will flash the green light within the stereoscope and generate a triple audible beep, which indicates that a satisfactory pull test has been achieved. The armed surgical needle product will be acceptable as long as the operator releases the suture and does not continue to pull on the suture for over 0.5 seconds.

At stage 226, the microprocessor evaluates how long the load test has been conducted. In one embodiment, the 0.5 second time limit is the maximum time for conducting the pull test. Once the 0.5 second time limit has been reached, the microprocessor obtains another signal from the load cell at stage 228. At this time, if there is an increase in the load detected as a result of the operator releasing the tension on the suture allowing the full weight of the upper section of the hinge to press down on the load cell, the inspection is complete and the armed surgical needle product is deemed acceptable (stage 230). At stage 232, if a load change is still detected, the operator is pulling the suture past the prescribed maximum time limit. As a result, the microprocessor generates a red light and an audible rejection buzzer sound at stage 234 to indicate that the length of the pull test has exceeded the maximum allowable time limit and the product should be discarded.

Figure 12A:
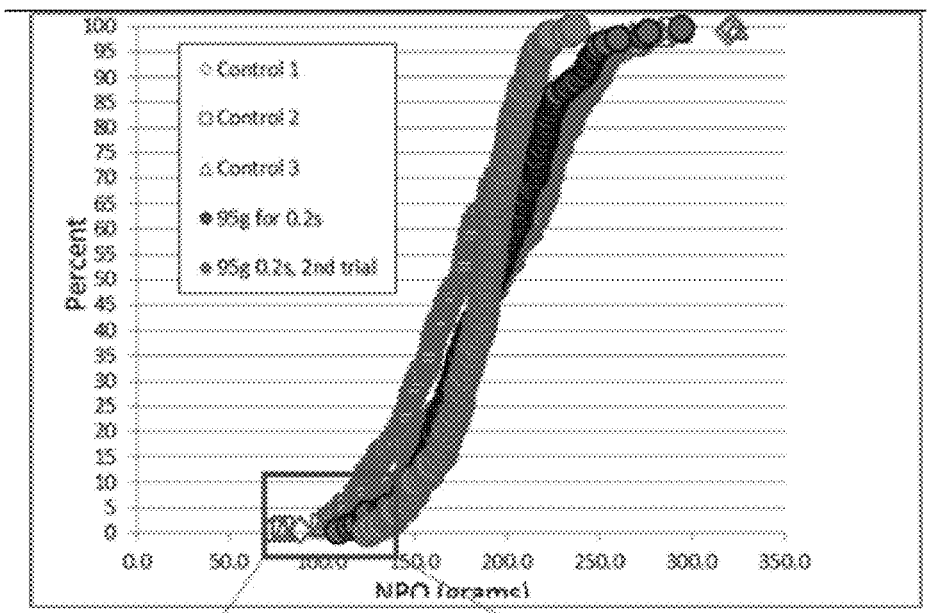
FIGS. 12A and 12B are graphs plotting data to indicate that the lower end of the attachment force population has been eliminated, in accordance with one embodiment of the present patent application.
Figure 12B:
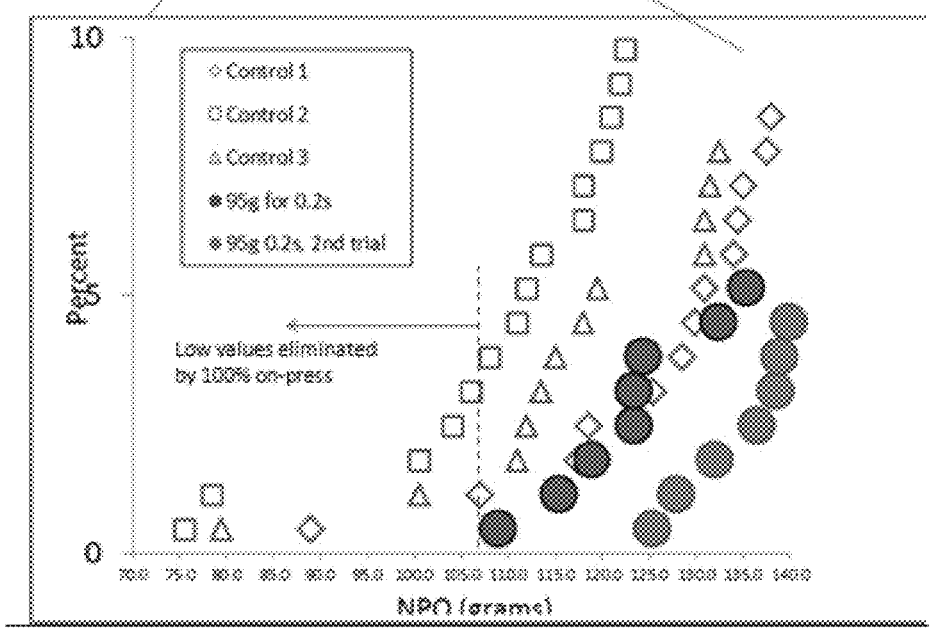

FIGS. 12A and 12B are graphs plotting Needle Pull-Off (NPO) data, which indicates that the lower end of the attachment force population has been eliminated by utilizing the swaging system, apparatus and methods disclosed herein.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A swaging system for attaching surgical needles to sutures and testing the attachment strength comprising:
a frame;
a bottom swaging die mounted on said frame;
a top swaging die mounted on said frame and being moveable up and down along a swaging axis that is in alignment with said bottom swaging die; and
said bottom swaging die comprising a hinge mechanism including a bottom plate mounted to said frame and a top plate overlying said bottom plate, wherein said top and bottom plates are pivotally connected to one another for enabling said top plate to pivot relative to said bottom plate, said bottom swaging die including a swaging tool mounted on said top plate that extends toward said top swaging die along the swaging axis, and a load cell disposed between said top and bottom plates for monitoring the load on said top plate.

2. The swaging system as claimed in claim 1, wherein said swaging tool includes an upper end having a top surface comprising a swaging notch for swaging a needle to a suture to form an armed surgical needle, and a testing notch, adjacent said swaging notch, for conducting a pull test on said armed surgical needle.

3. The swaging system as claimed in claim 2, wherein said swaging and testing notches extend along respective longitudinal axes that are orthogonal to the swaging axis.

4. The swaging system as claimed in claim 3, wherein said swaging and testing notches extend along respective longitudinal axes that are parallel with the top surface of said top plate and perpendicular to the swaging axis.

5. The swaging system as claimed in claim 2, wherein said swaging notch has a first width and said testing notch has a second width that is smaller than the first width, wherein said needle has a diameter that is less than or equal to the first width of said swaging notch and greater than the second width of said testing notch, and wherein said suture has a diameter that is less than the first width of said swaging notch and the second width of said testing notch.

6. The swaging system as claimed in claim 5, wherein the first width of said swaging notch is about 8 mil, the second width of said testing notch is about 4 mil, the diameter of said needle is about 7.5 mil, and the diameter of said suture is about 3.5 mil.

7. The swaging system as claimed in claim 2, further comprising a control system having at least one microprocessor in communication with said load cell for receiving load signals measured by said load cell, wherein said microprocessor is adapted for detecting changes in the load signals measured by said load cell.

8. The swaging system as claimed in claim 7, wherein said control system comprises one or more pull test programs stored therein for conducting pull tests on armed surgical needles, wherein each said pull test program includes an acceptable load range having predetermined lower and upper load limits, and an acceptable time range having predetermined lower and upper time limits.

9. The swaging system as claimed in claim 8, wherein each said pull test program enables a human operator to commence a pull test inspection when a load change is detected by said microprocessor, wherein each said pull test program indicates that the tested armed surgical needle is acceptable if the detected load change is between the predetermined lower and upper load limits and the detected time is between the predetermined lower and upper time limits, wherein each said pull test program indicates that the tested armed surgical needle is unacceptable if the detected load change is above the predetermined upper load limit, and wherein each said pull test program indicates that the tested armed surgical needle is unacceptable if the detected load change is between the predetermined lower and upper load limits and the detected time is above the predetermined upper time limit.

10. The swaging system as claimed in claim 9, wherein during a pull test inspection of an armed surgical needle said control system generates visible or audible signals that indicate whether said tested armed surgical needle is acceptable or unacceptable.

11. The swaging system as claimed in claim 10, wherein said control system generates visible green light and an audible beep if said tested armed surgical needle is acceptable and visible red light and an audible buzzer if said tested armed surgical needle is unacceptable.

12. A swaging system for attaching surgical needles to sutures and testing the attachment strength of armed surgical needles comprising:
a frame;
a bottom swaging die mounted on said frame;
a top swaging die mounted on said frame and being moveable up and down along a swaging axis that is in alignment with said bottom swaging die; and
said bottom swaging die comprising
a hinge mechanism including a bottom plate mounted to said frame,
a top plate overlying said bottom plate, wherein said top and bottom plates are pivotally connected to one another for enabling said top plate to pivot relative to said bottom plate,
a swaging tool mounted on said top plate that extends toward said top swaging die along the swaging axis, said swaging tool includes an upper end having a top surface with a swaging notch for swaging a needle to a suture to form an armed surgical needle, and a testing notch, adjacent said swaging notch, for conducting a pull test on said armed surgical needle, and
a load cell disposed between said top and bottom plates for monitoring the load on said top plate; and
a control system having at least one microprocessor in communication with said load cell for receiving load signals generated by said load cell and detecting changes in the load signals, wherein said control system comprises one or more pull test programs for conducting pull tests on armed surgical needles, wherein each said pull test program includes an acceptable load range having predetermined lower and upper load limits, and an acceptable time range having predetermined lower and upper time limits.

13. The swaging system as claimed in claim 12, wherein each said pull test program commences a pull test inspection when a load change is detected by said at least one microprocessor, wherein each said pull test program indicates that the tested armed surgical needle is acceptable if the detected load change is between the predetermined lower and upper load limits and the detected time is between the predetermined lower and upper time limits, wherein each said pull test program indicates that the tested armed surgical needle is unacceptable if the detected load change is above the predetermined upper load limit, and wherein each said pull test program indicates that the tested armed surgical needle is unacceptable if the detected load change is between the predetermined lower and upper load limits and the detected time is above the predetermined upper time limit.

14. The swaging system as claimed in claim 13, wherein during a pull test inspection of an armed surgical needle said control system generates visible or audible signals that indicate whether said tested armed surgical needle is acceptable or unacceptable.

15. The swaging system as claimed in claim 14, wherein said control system generates visible green light and a first audible sound if said tested armed surgical needle is acceptable and visible red light and a second audible sound if said tested armed surgical needle is unacceptable.

16. The swaging system as claimed in claim 14, further comprising a stereoscope mounted on said frame for viewing said swaging and inspection notches at the top surface of said swaging tool, wherein said stereoscope comprises at least one light emitting diode for generating said green visible light and said red visible light.

17. The swaging system as claimed in claim 12, wherein said hinge mechanism further comprises:
a pin interconnecting adjacent sides of said top and bottom plates for pivotally connecting said top and bottom plates;
said bottom plate comprising a guard located on a side of said bottom plate that is opposite said pin, wherein said guard has an upper end that extends above the top surface of said top plate for preventing an operator from inadvertently contacting the top surface of said top plate.

18. The swaging system as claimed in claim 12, wherein said bottom plate of said hinge mechanism has a recess and said load cell is disposed within said recess.

19. The swaging system as claimed in claim 18, wherein said load cell has an adjustable set screw projecting from an upper end of said load cell, and said top plate has a set screw opening accessible at the top surface of said top plate for accessing said set screw of said load cell.

20. A swaging system for attaching surgical needles to sutures and testing the attachment strength comprising:
a frame;
a bottom swaging die mounted on said frame;
a top swaging die mounted on said frame and being moveable up and down along a swaging axis that is in alignment with said bottom swaging die; and
said bottom swaging die comprising
a hinge mechanism including a bottom plate mounted to said frame,
a top plate overlying said bottom plate, wherein said top and bottom plates are pivotally connected to one another for enabling said top plate to pivot relative to said bottom plate,
a swaging tool mounted on said top plate that extends toward said top swaging die along the swaging axis, said swaging tool includes an upper end having a top surface with a swaging notch accessible at the top surface for swaging a needle to a suture to form an armed surgical needle, and a testing notch accessible at the top surface, adjacent said swaging notch, for conducting a pull test on said armed surgical needle, wherein said swaging and testing notches extend along respective longitudinal axes that are orthogonal to the swaging axis, and
a load cell disposed between said top and bottom plates for monitoring the load on said top plate.

\* \* \* \* \*